(12) United States Patent
Tai et al.

(10) Patent No.: US 10,492,945 B2
(45) Date of Patent: Dec. 3, 2019

(54) SMALL MOLECULE TRANSPORT DEVICE WITH ANTI-CONDENSATION FILLER FOR DRUG DELIVERY OR WASTE REMOVAL

(71) Applicant: California Institute of Technology, Pasadena, CA (US)

(72) Inventors: Yu-Chong Tai, Pasadena, CA (US); Nicholas Scianmarello, Pasadena, CA (US); Colin A. Cook, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/985,468

(22) Filed: May 21, 2018

(65) Prior Publication Data

US 2018/0333298 A1  Nov. 22, 2018

Related U.S. Application Data

(60) Provisional application No. 62/509,520, filed on May 22, 2017.

(51) Int. Cl.
*A61F 9/00* (2006.01)
*B29C 39/10* (2006.01)
(Continued)

(52) U.S. Cl.
CPC ............ *A61F 9/0017* (2013.01); *B29C 39/10* (2013.01); *B29C 41/36* (2013.01);
(Continued)

(58) Field of Classification Search
CPC .............. A61F 9/0017; A61F 2240/001; A61F 2250/0068; B29C 39/10; B29C 41/36; B29K 2083/005
See application file for complete search history.

(56) References Cited

U.S. PATENT DOCUMENTS

| 7,813,807 B2 | 10/2010 | Franklin et al. |
| 8,255,030 B2 | 8/2012 | Tapsak et al. |

(Continued)

FOREIGN PATENT DOCUMENTS

| CA | 2890417 | 4/2014 |
| CN | 102202708 | 9/2011 |

(Continued)

OTHER PUBLICATIONS

PCT/US2018/033733, "International Search Report and Written Opinion", dated Aug. 9, 2018, 9 pages.
(Continued)

*Primary Examiner* — Philip R Wiest
(74) *Attorney, Agent, or Firm* — Kilpatrick Townsend & Stockton LLP

(57) ABSTRACT

An implantable medical device is described. The implantable medical device includes an anti-condensation filler that is highly permeable to a predetermined class of small molecules, such as oxygen. The implantable medical device includes a small molecule discharge bag that is permeable to the small molecule, and a cannula that connects an interior of the small discharge bag to the anti-condensation filler. In operation, small molecules are collected and transported through the anti-condensation filler to the cannula for diffusion through the small molecule discharge bag. Even when this device is implanted in a high humidity and temperature gradient environment, the anti-condensation filler prevents condensation, such as water condensation.

20 Claims, 9 Drawing Sheets

(51) Int. Cl.
*B29C 41/36* (2006.01)
*B29K 83/00* (2006.01)
*B29L 31/00* (2006.01)

(52) U.S. Cl.
CPC . *A61F 2240/001* (2013.01); *A61F 2250/0068* (2013.01); *B29K 2083/005* (2013.01); *B29L 2031/7548* (2013.01)

(56) References Cited

U.S. PATENT DOCUMENTS

| | | |
|---|---|---|
| 9,763,825 B2 | 9/2017 | Tai et al. |
| 2006/0200097 A1 | 9/2006 | Humayun et al. |
| 2006/0247664 A1 | 11/2006 | Meng et al. |
| 2008/0039792 A1 | 2/2008 | Meng et al. |
| 2008/0046028 A1 | 2/2008 | Franklin et al. |
| 2008/0262611 A1 | 10/2008 | Li et al. |
| 2009/0192493 A1 | 7/2009 | Meng et al. |
| 2009/0240215 A1 | 9/2009 | Humayun et al. |
| 2009/0306585 A1 | 12/2009 | Pang et al. |
| 2009/0306594 A1 | 12/2009 | Pang et al. |
| 2010/0168646 A1 | 7/2010 | Greenbaum et al. |
| 2010/0168648 A1 | 7/2010 | Kost et al. |
| 2012/0041427 A1 | 2/2012 | Caffey et al. |
| 2013/0116665 A1 | 5/2013 | Humayun et al. |
| 2013/0150775 A1 | 6/2013 | Dos et al. |
| 2014/0058506 A1 | 2/2014 | Tai et al. |
| 2014/0200553 A1 | 7/2014 | Johnson et al. |
| 2014/0228660 A1 | 8/2014 | Mujeeb-u-rahman et al. |
| 2015/0273197 A1 | 10/2015 | Humayun et al. |
| 2015/0366707 A1 | 12/2015 | Tai et al. |
| 2017/0071785 A1* | 3/2017 | Tai ..................... A61N 1/3787 |

FOREIGN PATENT DOCUMENTS

| | | |
|---|---|---|
| CN | 104902846 | 9/2015 |
| WO | 2006014793 | 2/2006 |
| WO | 2014055989 A1 | 4/2014 |
| WO | 2016164406 | 10/2016 |
| WO | 2017044839 A1 | 3/2017 |

OTHER PUBLICATIONS

White et al., "Single Ion-Channel Recordings Using Glass Nanopore Membranes", Journal of the American Chemical Society, vol. 129, No. 38, Sep. 26, 2007, pp. 11766-11775.

Efron et al., "Oxygen Levels Beneath the Closed Eyelid", nvest. Ophthalmol. Visual Sci., vol. 18, No. 1, Jan. 1979, pp. 93-95.

Kang et al., "MEMS Oxygen Transporter to Treat Retinal Ischeimia", California Institute of Technology, Pasadena.

Klein , "Overview of Epidemiologic Studies of Diabetic Retinopathy", Opthalmic Epidemiology, vol. 14, Jul.-Aug. 2007, pp. 179-183.

McLeod , "Krogh Cylinders in Retinal Development, Panretinal Hypoperfusion and Diabetic Retinopathy", Acta Ophthalmologica, vol. 88, 2010, pp. 817-835.

PCT/US2016/051090, "International Search Report and Written Opinion", dated Nov. 29, 2016, 6 pages.

U.S. Appl. No. 15/261,435, "Notice of Allowance," dated May 10, 2017, 13 pages.

U.S. Appl. No. 15/261,435, "Supplemental Notice of Allowance," dated Jun. 15, 2017, 4 pages.

Narhe et al., Water Condensation on a super-hydrophobic spike surface, Europhys. Lett., 75(1), pp. 98-104, 2006.

Enright, et al., Condensation on Superhydrophobic Surfaces: The Role of Local Energy Barriers and Structure Length Scale, Langmuir 28(40), pp. 14424-14432, Oct. 9, 2012.

* cited by examiner

SMALL MOLECULE TRANSPORT DEVICE WITH ANTI-CONDENSATION FILLER FOR DRUG DELIVERY OR WASTE REMOVAL

CROSS-REFERENCES TO RELATED APPLICATIONS

This application claims the benefit of U.S. Provisional Application No. 62/509,520, filed May 22, 2017, which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant No. EY022059 awarded by the National Institutes of Health. The government has certain rights in the invention.

BACKGROUND

1. Field of the Art

Generally, embodiments of the present invention relate to methods and devices for treatment of the eyes and other areas within the body. More specifically, embodiments relate to implantable devices that include anti-condensation fillers and that are used for capturing small molecule therapeutic agents or waste material and transporting them to and from structures within the body.

2. Description of the Related Art

In the United States, a leading cause of blindness is diabetic retinopathy. Diabetic retinopathy is caused by retinal ischemia, that is, inadequate blood flow to the retina caused by capillary nonperfusion. The lack of capillary blood flow starves the retina of oxygen. Retinal vein occlusion also occurs in which small veins that move blood away from the retina are blocked. A subject with retinopathy loses vision over time as retinal cells in his or her eyes die.

Other areas of the body besides the eyes can experience lack of blood flow caused by diabetes or other ailments. Restriction of blood flow to a particular portion of the body is simply called ischemia. Ischemia is often accompanied by hypoxia, which refers to the lack of oxygen ($O_2$) that blood delivers. Ischemic insults often cause severe tissue hypoxia and ultimately tissue death.

Current treatment methods for ischemic diseases are limited and do not necessarily treat the primary cause of the disease—that is, hypoxia. The mainstay of treatment for capillary nonperfusion or areas of ischemia is laser ablation. This treatment is destructive, irreversible, and can cause additional organ loss. Systemic administration of oxygen is also an option, but toting around pure oxygen or scheduling appointments for oxygen injections carries risks and is inconvenient for subjects.

Retinal ischemia can be treated with the above methods, but such treatments in the eye carry additional drawbacks. For example, laser ablation and photocoagulation can result in a constricted peripheral visual field as well as delayed dark adaptation. Other treatments have been developed for the eye, such as intravitreal injections and pars plana vitrectomies. Intravitreal injections often need to be repeated frequently and poses significant risk and cost to the patient and healthcare system. Intravitreal injections use therapeutic agents that only suppress downstream effects of the hypoxia on retinal tissue. A pars plana vitrectomy, which removes a portion of vitreous humor from the eye, may result in insufficient amounts of retinal oxygen while causing cataracts or other potential oxygen toxicity near the lens. Indeed, too much oxygen near the front (anterior) inside of the eyeball near the lens is a bad thing. It can also increase the risk of iris neovascularization as well as elevated intraocular pressure.

Therefore the current armamentarium of treatments for ischemic retinal and other diseases has a number of distinct disadvantages that need to be overcome.

BRIEF SUMMARY

Generally described is a biocompatible, implantable medical device. In some embodiments, the device may include a collection and transport element comprising an anti-condensation filler, a permeable coating, and a nonpermeable coating. The anti-condensation filler is permeable to a predetermined class of small molecules and comprises a base and an elongated body extending from the base. The permeable coating is permeable to the small molecules and is over at least a portion of an external surface of the base. The nonpermeable coating is nonpermeable to the small molecules and is over at least a portion of an external surface of the elongated body. The device also includes a cannula comprising a lumen and a small molecule discharge bag comprising an interior. At least a portion of the small molecule discharge bag is permeable to the small molecules. The lumen of the cannula connects the elongated body of the anti-condensation filler with the interior of the small molecule discharge bag.

In an example, the anti-condensation filler comprises a nano-porous material and the predetermined class of small molecules comprises oxygen. The nano-porous material can include a nano-porous glass that is hydrophobized based on silanization, where the base and the elongated body are integrally formed with the nano-porous glass. The nano-porous glass comprises pores having an average width within a range of four to twenty nanometers. A density of the pores is in the range of twenty to fifty percent.

In an example, the base is substantially cylindrical and has a first height and a first diameter. The elongated body is also substantially cylindrical and has a second height and a second diameter. The first height is smaller than the second height and the first diameter is larger than the second diameter. For instance, the first height is between 0.5 and 1.5 millimeters and the first diameter is between three and four millimeters. In comparison, the second height is between two and four millimeters and the second diameter is between 0.5 and 2.5 millimeters.

In an example, the base and the elongated body are integrally formed in substantially a T-shaped tack. The base corresponds to a cylindrical head of the T-shaped tack and the elongated body corresponds to a cylindrical shaft of the T-shaped tack.

Some embodiments are related to a method of manufacturing a biocompatible, implantable medical device. The method can include spreading uncured, biocompatible silicone on a first half mold. The method can also include placing the nano-porous glass in a first portion of the first half mold, the nano-porous glass comprising a base and an elongated body extending from the base, the nano-porous glass hydrophobized based on silanization. The method can also include partially curing the uncured, biocompatible silicone on the first half mold that contains the nano-porous glass. The method can also include aligning a partially cured second half mold with the partially cured first half mold that contains the nano-porous glass. The method can also include further curing the partially cured second half mold and the partially cured first half mold to create an integrally formed workpiece that contains the nano-porous glass, a sac, and a cannula that connects the nano-porous glass and the sac. The method can also include masking a first portion and a second portion of the workpiece, the first portion corresponding to at least the base of the nano-porous glass, and the second portion corresponding to the sac. The method can also include depositing parylene on the workpiece.

Some embodiments are related to a method of surgically implanting a medical device. The method can include obtaining an implantable medical device comprising an anti-condensation filler. The anti-condensation filler comprises a nano-porous material that is hydrophobic or has been hydrophobized. The method can also include placing a first portion of the anti-condensation filler in a first environment. The method can also include placing a second portion of the anti-condensation filler in a second environment. The second environment has a higher humidity relative to the first environment. A temperature differential exists between the first environment and the second environment. In an example, the first portion corresponds to a base of the anti-condensation filler and the second portion corresponds to an elongated body of the anti-condensation filler extending from the base. In this example, the base is placed between a conjunctiva and sclera of an eyeball and the elongated body is placed inside the eyeball.

A further understanding of the nature and the advantages of the embodiments disclosed and suggested herein may be realized by reference to the remaining portions of the specification and the attached drawings.

DETAILED DESCRIPTION

Figure 1:
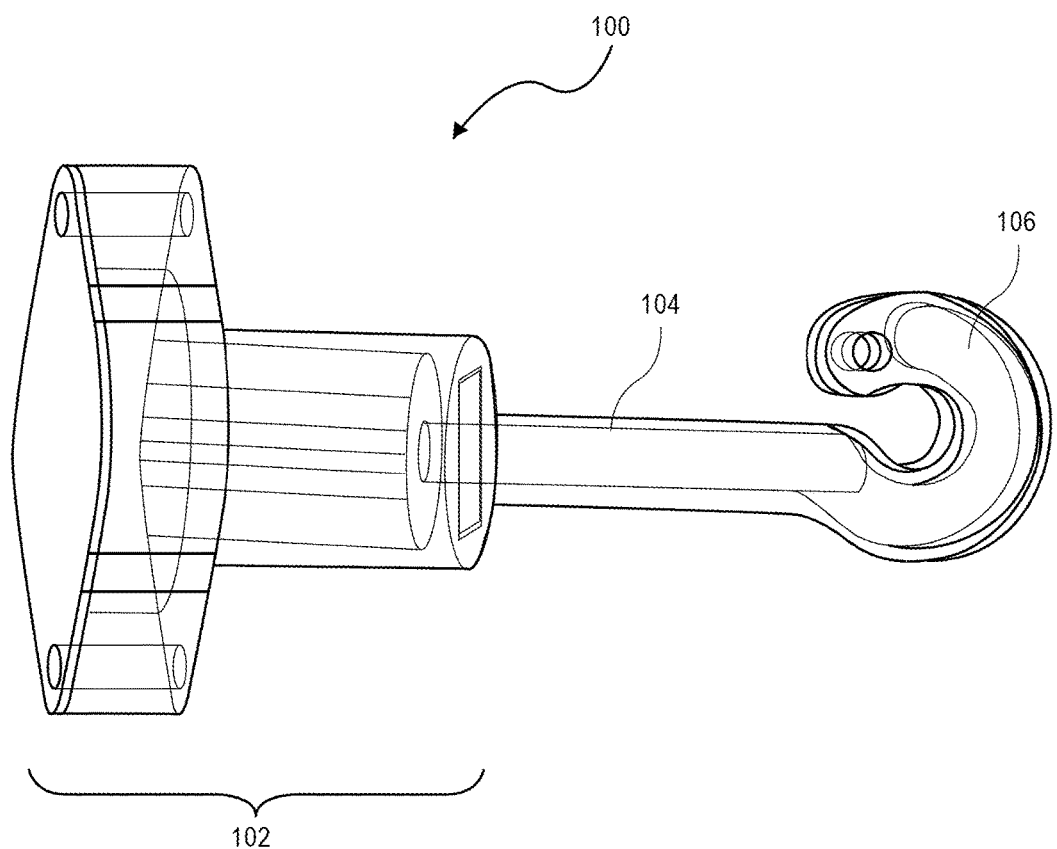
FIG. 1 illustrates a device, in accordance with an embodiment.

Medical devices, their methods of manufacture, and surgical methods for their implantation are described. The medical devices capture, in the body, any biologically or chemically active agent that may have therapeutic benefits. They then deliver the agent to another part of the body. The device can also be used for removing waste or any non-therapeutic material from one area of the body to another.

Particularly described is an exemplary device to treat ischemic retinal diseases by passively supplying oxygen. The device transports oxygen from an oxygen-rich zone into an oxygen deficient one based on a natural concentration gradient. In an example case of retinal ischemia, this can be from the subconjunctival space into the vitreous cavity. This may prevent a further decline of vision, avoid laser photocoagulation, and possibly avoid a pars plana vitrectomy.

U.S. Pat. Nos. 9,655,774, 9,763,825, and 9,919,140, which are owned by applicant, describe implantable medical devices for delivering, among other agents, oxygen through passive and/or active oxygen delivery. The disclosures of the U.S. Pat. Nos. 9,655,774, 9,763,825, and 9,919,140 are incorporated herein by reference in their entireties.

In comparison, an embodiment of the present invention can also treat ischemia through passive and/or active oxygen delivery to an ischemic or deficient region. The embodied implantable medical device includes, among other elements such as a cannula and a discharge bag, a filler that prevents condensation of water and that is highly permeable to oxygen. The filler forms a collection and transport element. This element can be implanted in the eye, where a first portion of the element can be placed between the eye's conjunctiva and sclera, and where a second portion of the element (e.g. the remaining portion) can pierce through the sclera. The first portion is in an oxygen rich environment at room temperature and includes an inlet surface permeable to oxygen, thereby allowing collection of oxygen. The second portion is in an oxygen deprived environment at a different temperature (e.g., thirty-seven degrees Celsius) and includes an outlet surface permeable to oxygen, thereby allowing diffusion of the oxygen into, for example, a lumen of the cannula. Remaining surfaces of the collection and transport element are impermeable to the oxygen, thereby avoiding undesired diffusion of oxygen through these surfaces. The filler includes material that prevents water condensation while allowing a high rate of oxygen transport, such as a nano-porous glass that has been hydrophobized.

Generally, condensation, such as water condensation, can be a problem in several applications where there is high humidity and a temperature gradient. As the temperature drops in any air chamber, water vapor concentration can exceed 100% relative humidity. At this point, water can condense against any nucleation site. This condensation can limit small molecule (e.g., oxygen) transport and delivery in devices subject to the high humidity and temperature gradient, thereby significantly reducing the performance of the devices when in use.

One approach to avoid condensation is to ensure a complete hydrophobic coating on the internal surface of a device, thereby preventing surface water adsorption. However, any defect in these surfaces is a nucleation site which leads to condensation. It is impractical to have a perfect surface. Indeed literature, such as "Condensation on superhydrophobic surfaces: The role of local energy barriers and structure length-scale," by R. D. Narhe and D. A. Beysens, published in Europhys. Lett., 75 (1), pp. 98-104 (2006), shows increased condensation in superhydrophobic surfaces.

In contrast, the above described filler is designed as an anti-condensation filler that is also highly permeable to oxygen (or other small molecule gases), thereby avoiding water condensation and transporting oxygen even when the device is subject to the high humidity and temperature gradient. In the example of a hydrophobized nano-porous material, the nano size of the pores provides permeability and open pore structure to transport oxygen. The porosity of the material supports a particular permeability rate. The surfaces of the pores are hydrophobic (based on the hydrophobization of the glass) and prevent the condensation.

The potential for water condensation can be better understood by the Kelvin equation. The Kelvin equation relates a vapor pressure above a liquid droplet to a saturation pressure in the medium. This is equivalent to looking at the relative humidity/100 (vapor pressure/saturation pressure) of water. The Kelvin equation is expressed as:

$$\frac{p}{p_{sat}} = \frac{2\gamma V_m}{rRT}$$

where p is the vapor pressure, $p_{sat}$ is the saturation pressure, $\gamma$ is the surface tension, r is the radius of the water droplet, R is the gas constant, T is the temperature, and $V_m$ is the molar volume.

At nanoscopic sizes, above 100% relative humidity is needed for condensation. If one can restrict the region in which water can condense to be smaller than the minimum size required to form a droplet in the expected relative humidity of the environment, it is possible to prevent condensation above 100% relative humidity. It would make it energetically unfavorable for water to condense. This is the case assuming the enclosing material has a hydrophobic surface to prevent water adsorption on the surface. The pore sizes are typically below 20 nm in diameter (e.g., the pores have an average width within a range of four to twenty nanometers) and the porosity ranges from 20-50% (e.g., a density of the pores is in the range of twenty to fifty percent), depending on the expected relative humidity. Hence, the anti-condensation filler includes a material with small enough pores and a hydrophobic surface.

In an example, the nano-porous material includes one of glasses and silica. For these materials, hydrophobizing processes can be used to turn the surface from hydrophobic to above 90° contact angle. A silanization process can be used to achieve a hydrophobic coating by substituting hydroxyl groups with hydrophobic functional groups. Vycor 7930 (a VYCOR material available from Corning, Inc. of New York, U.S.A.) and other nano-porous glasses such as CoralPor 1000 (a CORALPOR material available from Schott AG of Mainz, Germany) have pore sizes within the appropriate range. Fumed silica particulates can be found with the appropriate pore distribution as well. These can be jointed in a substrate such as silicone, creating a composite material with strong mechanical properties (fused silica is a stiffener for silicone), while achieving high gas transport.

In another example, the nano-porous material is made of certain nano-porous polymers that can be naturally hydrophobic, such as expanded polytetrafluoroethylene (PTFE). Other materials are also possible, such perfluorocarbons (PFCs), synthetic blood enclosed in an appropriate container (e.g., a container having walls made of a nano-porous glass that has been hydrophobized).

In a further example, the same material used in the anti-condensation (e.g., hydrophobized Vycor 7930 or another nano-porous material having hydrophobic surfaces (e.g., expanded PTFE)) can also be used as fillers in other volumes that need to remain open for the transport of gases. For instance, the cannula and/or the discharge bag can contain any of such materials.

FIG. 1 illustrates a device 100, in accordance with an embodiment. The device 100 is comprised of a collection and transport element 102, a nonpermeable cannula 104, and a permeable discharge bag 106. The collection and transport element 102 collects oxygen from an oxygen rich zone. The cannula 104 is a tube to transport the oxygen. The discharge bag 106 releases or diffuses the oxygen to a targeted region.

The collection and transport element 102, cannula 104, and discharge bag 106 are made of or coated with biocompatible silicone that forms one or more permeable membranes. An impermeable coating (e.g., metallization of the surface, Parylene coating such as Parylene C, Parylene HT, Parylene D, or Parylene N coating, epoxy, etc.) surrounds particular portions of the external surfaces of the collection and transport element 102 and, optionally, the cannula 104, thereby forming nonpermeable membranes and lowering the permeability of these portions to the point of non-permeability. Parylene is a biocompatible polymer with a permeability rate that is five orders of magnitude lower than silicone. The coatings and resulting membranes are further illustrated in the next figures.

"Permeability" of a material is typically in relation to a size of substance of interest. A Stokes-Einstein radius or a Stokes diameter is a measure of the diffusion properties of a substance. A "Stokes diameter" is an equivalent diameter of a hard sphere that a molecule possesses in terms of its diffusion rate. A molecule can pass through thin materials with pores that have a Stokes diameter that is about 1 to about 5 times the Stokes diameter of the molecule.

"About" includes within a tolerance of ±0.01%, ±0.1%, ±1%, ±2%, ±3%, ±4%, ±5%, ±8%, ±10%, ±15%, ±20%, ±25%, or as otherwise known in the art.

Drug (e.g., oxygen) diffusion out of the discharge bag 106 into a deficient region of the body lowers the device's internal concentration, and this in turn pulls oxygen from an oxygen rich region into the device. The concentration gradient will continue to transport oxygen from the outside of the eye to the inside of the vitreous cavity.

Bubble formation on the external surface of the device 100 can be prevented by performing hydrophobic and hydrophilic external surface modifications. This can prevent gas accumulation on the surface and allow for only the dissolved drug to be delivered.

Dosing and targeted release can be controlled by material properties of the device. Controlling the thickness of silicone can determine the permeation rate (dosing). The same thickness of silicone can be used in the silicone coatings for the collection and transport element 102, cannula 104, and discharge bag 106. Hence, a single adjustment to how much silicone is distributed on a mold can determine a permeation rate. The parylene C coating can be deposited at the particular portions to form inlet and outlet surfaces for collecting and transporting oxygen.

The sizes and shapes of the collection and transport element 102 and discharge bag 106 can also be adjusted to alter the permeation rate. These sizes and shapes are application dependent and can be designed for the specific task the device is to perform.

Other small molecules besides diatomic oxygen can also be captured and transported. The device can be targeted for carbon dioxide ($CO_2$), nitrous oxide ($N_2O$), water, or other gases.

Figure 2:
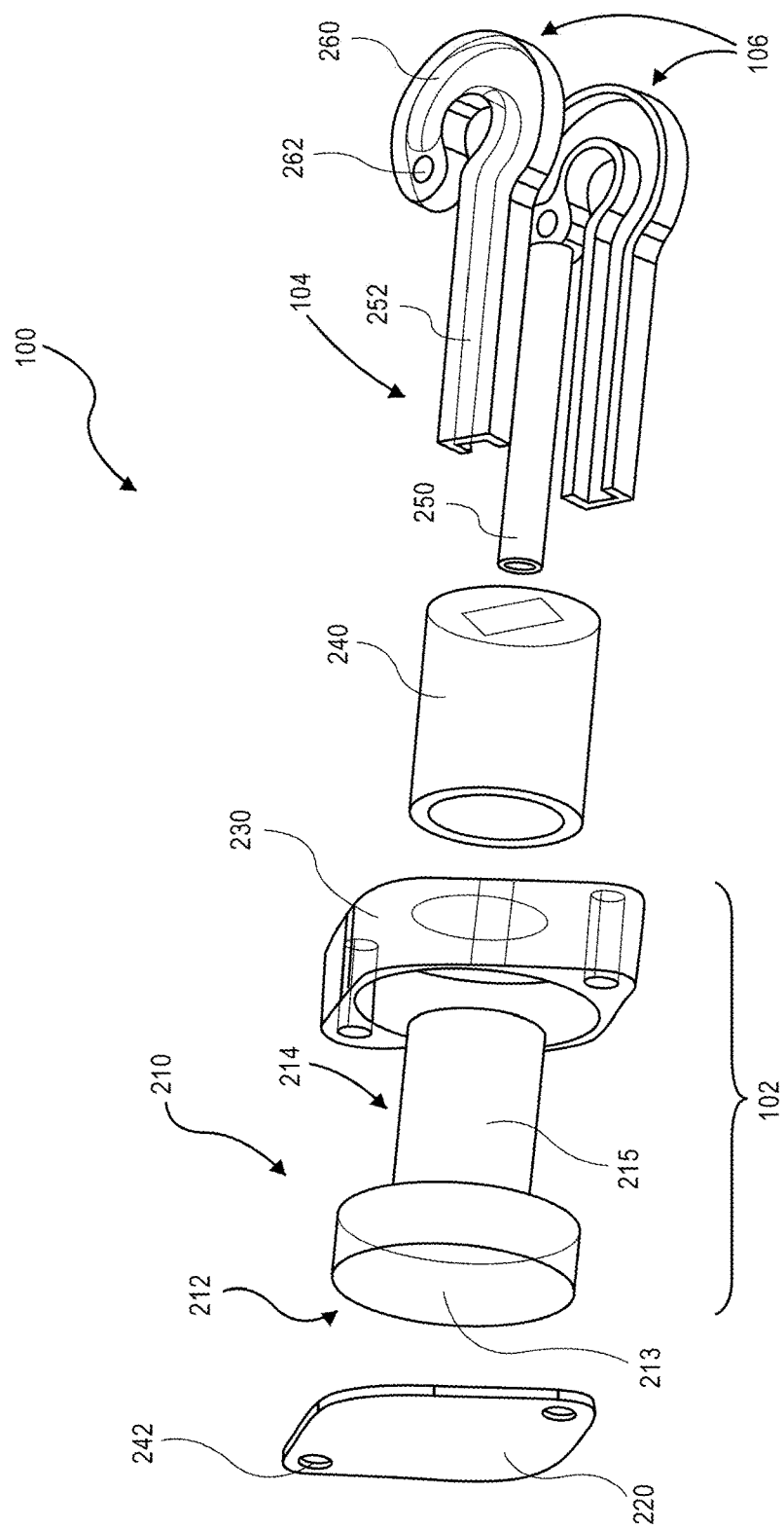
FIG. 2 illustrates an assembly of a device, in accordance with an embodiment.

FIG. 2 illustrates an assembly of the device 100, in accordance with an embodiment. As illustrated, the collection and transport element 102 includes an anti-condensation filler 210, a permeable coating 220, a first nonpermeable coating 230, and a second nonpermeable coating 240. The anti-condensation filler 210 prevents water condensation while being highly permeable to a predetermined class of small molecules, such as oxygen. For example, the anti-condensation filler 210 includes a nano-porous material, such as a nano-porous glass (e.g. Vycor 7930) that was hydrophobized. This material or, similarly, the anti-condensation filler 210 is shaped and sized to have a base 212 and an elongated body 214 extending from the base 212. The permeable coating 220 is permeable to the small molecules (e.g., oxygen) and is over at least a portion of an external surface 213 of the base 212, when the collection and transport element 102 is assembled. The first nonpermeable coating 230 is nonpermeable to the small molecules and is over at least a different portion of the external surface 213 of the base 212, when the collection and transport element 102 is assembled. The second nonpermeable coating 240 is also nonpermeable to the small molecules and is over at least a portion of an external surface 215 of the elongated body 214, when the collection and transport element 102 is assembled.

In an embodiment, the base 212 and the elongated body 214 are integrally formed with the same material (e.g., the nano-porous glass such as the hydrophobized Vycor 7930). This material includes nano-pores having an average width of ten nanometers and a porosity of about thirty percent.

Generally and upon implantation of the device 100, the base 212 remains securely in place outside the eye (e.g., within subconjunctival space) while the elongated body 214 is placed inside the eye (e.g., the vitreous space). To avoid the risk of slipping into the eye (e.g., into the vitreous space), the base 212 has a width larger than a width of the elongated body 214. Generally, the elongated body 214 has a length larger than a length of the base 212. For example, the base 212 is substantially cylindrical and has a first diameter (e.g., a width) and a first height (e.g., a length). The elongated body 214 is also substantially cylindrical and has a second diameter and a second height. The first diameter is larger than the second diameter and the first height is smaller than the second height. For instance, the first diameter is between one and fifteen millimeters and the first height is between 0.1 and two millimeters. In comparison, the second diameter is between 0.05 and three millimeters and the second height is between one and twenty-five millimeters.

In an example, the base 212 and the elongated body 214 are integrally formed in substantially a T-shaped tack. The base 212 corresponds to a cylindrical head of the T-shaped tack. The elongated body 214 corresponds to a cylindrical shaft of the T-shaped tack. In this example, the height and diameter of the base 212 are about one millimeter and 3.7 millimeters, respectively. The height and diameter of the elongated body 214 are about three millimeters and 1.5 millimeters, respectively. The base 212 and the elongated body 214 are centered around a same axis.

The coatings 220-240 are applied to the anti-condensation filler 210 to specifically form an inlet surface and an outlet surface, such that oxygen (or the targeted small molecules) are collected through the inlet surface, transported through the anti-condensation filler 210, and discharged through the outlet surface. Collection may include absorption and/or diffusion based on permeability of a surface, a membrane, and/or a material. Accordingly, the inlet surface and outlet surface each corresponds to a permeable membrane (e.g., a membrane permeable to oxygen), while remaining external surfaces of the collection and transport element 102 correspond to nonpermeable membranes (e.g., membranes nonpermeable to oxygen).

In an example, the permeable coating 220 is a silicone coating formed by depositing and curing silicone on the open face of the base 212 (e.g., the outside planar surface having a circular shape of the external surface 213) or any external surface of the base 212 that is expected to be in an oxygen rich environment when the device 100 is implanted. For instance, the silicone is NuSil Technology LLC (of Carpinteria, Calif., U.S.A.) MED4-4210, two-part, medical grade silicone in which base and curing agent are mixed at a 10:1 ratio by weight. The permeable coating 220 and this outside planar surface of the base 212 form the inlet surface (or, similarly, the permeable coating forms a permeable inlet membrane attached to the outside planar surface).

In comparison, the first nonpermeable coating 230 includes a parylene C coating forming a nonpermeable membrane around the remaining portions of the external surface 213 of the base 212. As further illustrated in the next figures, the parylene C coating can be deposited over a silicone coating that, in turn, is deposited over the remaining portion of the external surface 213 (e.g., this silicone coating can be of the same type and have a same thickness as the permeable coating 220, and can be formed during the same deposition and curing operations for forming the permeable coating 220).

Similarly, the second nonpermeable coating 240 includes a parylene C coating forming a nonpermeable membrane around the external surface 215 of the elongated body, with the exception of an outlet portion of the external surface that corresponds to the outlet surface. This outlet portion remains uncoated or may be coated with a permeable coating, such as silicone. An end of the cannula 104 attaches or connects to this permeable outlet portion of the external surface 215 such that oxygen can diffuse from the collection and transport element 102 into the lumen of the cannula 104 through this outlet portion. As further illustrated in the next figures, the parylene C coating can be deposited over a silicone coating that, in turn, is deposited over the full external surface 215 or over the external surface 215 minus its outlet portion. Here also, this silicone coating can be of the same type and have a same thickness as the permeable coating 220, and can be formed during the same deposition and curing operations for forming the permeable coating 220. In this example, the permeable coating 220 is not limited to the external surface 230 of the base 212 but also is deposited over the external surface 215 of the elongated body 214 except for the outlet surface and is beneath the second nonpermeable coating 240 (and beneath the first nonpermeable coating 230).

In an embodiment, the cannula 104 includes a lumen. The lumen of the cannula 104 connects the elongated body 214 of the anti-condensation filler 210 with an interior of the discharge bag 106. For instance, an end of the cannula 104 attaches or connects to the outlet portion of the external surface 215 of the elongated body 214. Another end (e.g., the opposite end) of the cannula 104 attaches or connects to the interior of the discharge bag 106.

In an example, the cannula 104 includes a tube 250 that has the lumen. For instance, this tube 250 is a biocompatible stainless steel tube and is pliable so that it can be bent and keep its bent shape. The external surface of the tube 250 can be coated with, for example, a permeable coating 252 and/or a nonpermeable coating (e.g., a parylene C coating). Here also, this permeable coating 252 can be of the same type and have a same thickness as the permeable coating 220, and can be formed during the same deposition and curing operations for forming the permeable coating 220.

In another example, the cannula 104 does not include the tube. Instead, a nonpermeable coating (e.g., a parylene C coating) forms a nonpermeable membrane that defines the cannula 104 and its lumen. This nonpermeable coating can be deposited over the silicone coating 252 (assuming no tube). And any of the nonpermeable coating or the permeable coating 252 can include a biocompatible metal strip that may be a thin metal foil, sheet, or solid rod. This strip can be bent by a surgeon's hands or by surgical instruments.

In an embodiment, the discharge bag 106 is a small molecule discharge bag that includes an interior. At least a portion of the small molecule discharge bag is permeable to the small molecules (e.g., oxygen). In an example, the discharge bag 106 has a particular shape (e.g., a hook, toroidal (i.e., ring), or any other shape) and is made out of a permeable material (e.g., material permeable to the small molecules). For instance, a permeable coating 260 forms a permeable membrane that defines the interior of the discharge bag 106 (in other words, the permeable coating 260 is over an external surface of the small molecule discharge bag). Here also, the permeable coating 260 can be of the same type and have a same thickness as the permeable coating 220, and can be formed during the same deposition and curing operations for forming the permeable coating 220.

In an embodiment, each, some, or one of the collection and transport element 102, the cannula 104, and the discharge bag 106 includes a retaining mechanism for securely retaining the device 100 in place once implanted. FIG. 2 illustrates an example of this retaining mechanism. In particular, a suturing holes(s) 242 can be formed in the collection and transport element 102, such as in any or a combination of the coatings 220, 230, 240, and 252. Similarly, a suturing hole(s) 262 can be formed in the discharge bag 106, such as in the permeable coating 260. The walls of such holes may be made out of the material found in the corresponding coatings. Other types of retaining mechanism are possible including, for example, foldable arms that can be rolled and extended out from the base 212 (e.g., from the sides of the cylinder that form the base 212).

Figure 3:
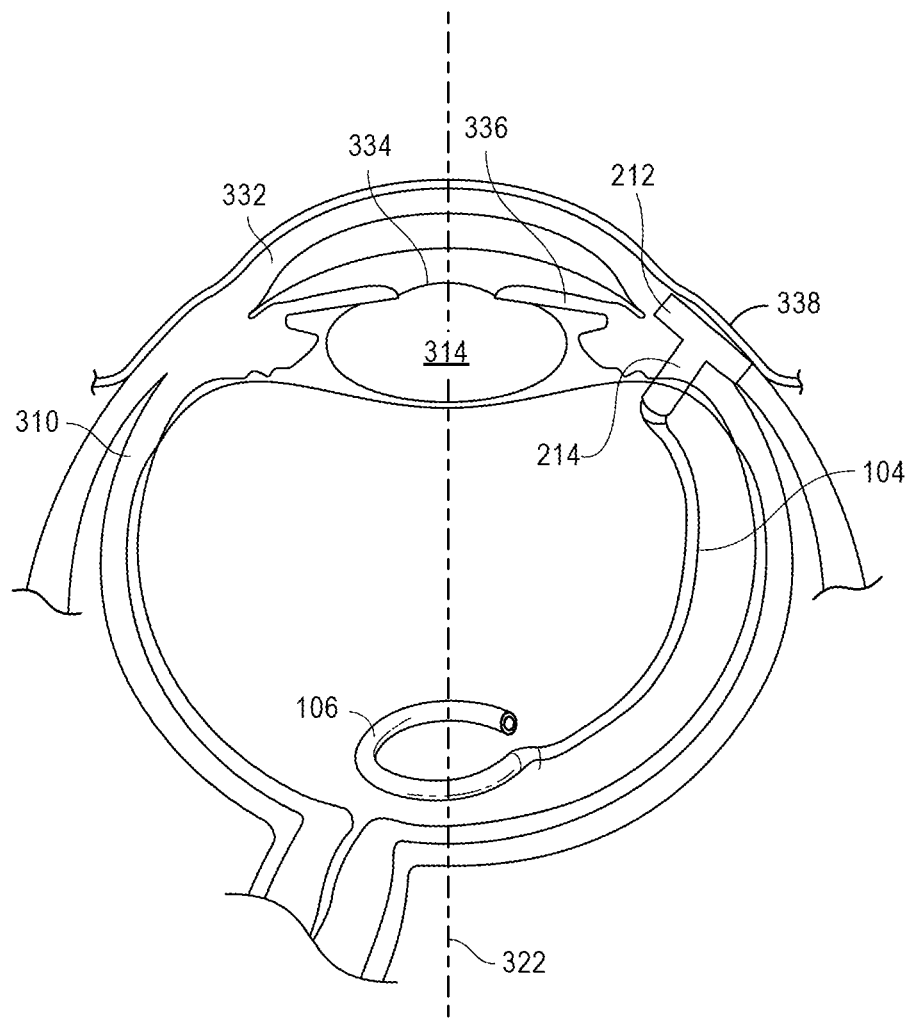
FIG. 3 illustrates an example of placing a device such that a particular oxygen flow is achieved in proximity of a targeted tissue, in accordance with an embodiment.

FIG. 3 illustrates an example of placing the device 100 such that a particular oxygen flow is achieved in proximity of a targeted tissue, in accordance with an embodiment. As illustrated, the base 212 of the anti-condensation filler 210 of the device 100 is placed in a subconjunctival space of an eyeball. To the side of lens 314, cornea 332, pupil 334, and iris 336, the base 212 sits under conjunctiva 338. At least a portion of the elongated body 214 of the anti-condensation filler 210 and/or the cannula 104 pierce sclera 310. The cannula 104 turns to the rear and ends up near the retina. The discharge bag 106 connects with cannula 104 such that the anti-condensation filler 210 is connected in a constant fluid path to the interior of discharge bag 106. The discharge bag 106 is positioned such that it is symmetrically placed around an optical axis 322, where the optical axis 322 is centered through the macula and the lens 314. Thus, the discharge bag 106 substantially surrounds the macula without obstructing it.

The above anti-condensation filler has been described in connection with transporting oxygen (or other small gas molecules). Nonetheless, the anti-condensation filler can be used for other applications by, for example, varying the type of coatings such that the small molecules, water vapor, or other agents can move from the base to the elongated body or in the opposite direction.

Figure 4:
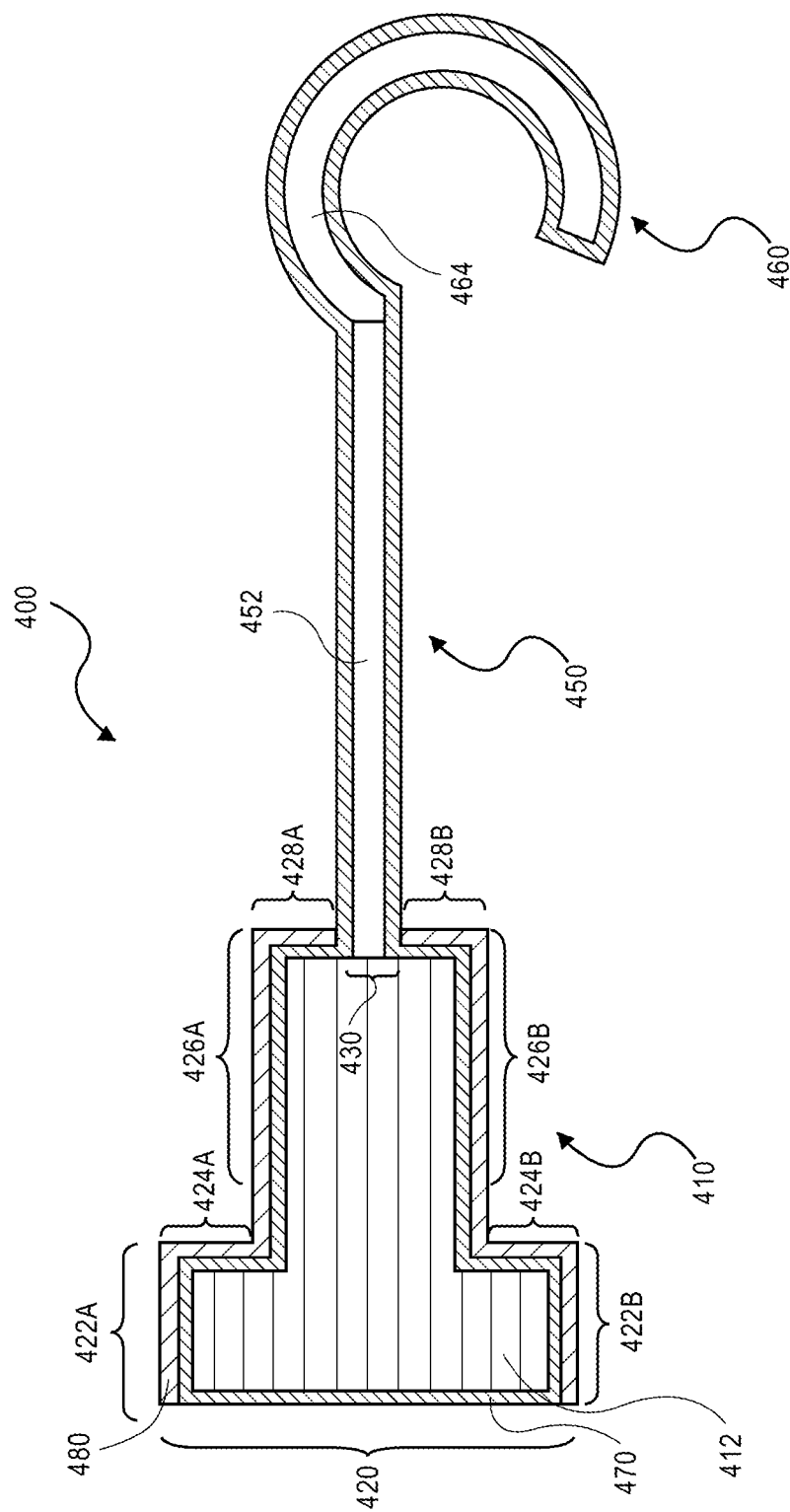
FIG. 4 illustrates a top view of an implantable medical device, in accordance with an embodiment.

FIG. 4 illustrates a top view of an implantable medical device 400, such as the device 100, in accordance with an embodiment. As illustrated, the implantable medical device 400 includes a collection and transport element 410, a cannula 450, and a discharge bag 460. The collection and transport element 410 includes an anti-condensation filler 412. A lumen 452 of the cannula 450 connects an elongated body of the anti-condensation filler 412 with an interior 464 of the discharge bag 460.

In an example, the anti-condensation filler 412 includes a base and the elongated body extending from the base. Various external surfaces define the base and the elongated body. These external surfaces include an inlet surface 420, side surfaces 422A and 422B, shoulder surfaces 424A and 424B, elongated surfaces 426A and 426B, cannula-facing surfaces 428A and 428B, and an outlet surface 430. The inlet surface 420, side surfaces 422A and 422B, and shoulder surfaces 424A and 424B are external surfaces that define the base. The elongated surfaces 426A and 426B, cannula-facing surfaces 428A and 428B, and outlet surface 430 are external surfaces that define the elongated body.

The lumen 452 of the cannula interfaces with the outlet surface 430 of the elongated body.

The anti-condensation filler 412 (potentially with the exception of the outlet surface 430), the cannula 450, and the discharge bag 460 are coated externally with permeable coating 470, such as a silicone coating, that forms a permeable membrane. Portions of the external surface of the anti-condensation filler 412 and, optionally, the cannula 450 are further coated with a nonpermeable material coating, such as a parylene C coating, that forms a nonpermeable membrane that sits over the permeable membrane.

In an example, the nonpermeable coating 480 is deposited over the permeable coating 470 having locations corresponding to the side surfaces 422A and 422B, shoulder surfaces 424A and 424B, elongated surfaces 426A and 426B, and cannula-facing surfaces 428A and 428B, but not to the locations corresponding to the inlet surface 420 and outlet surface 430. As such, oxygen (or some other small molecules) can flow into the anti-condensation filler 412 through the inlet surface 420 and the portion of the permeable coating 470 at that surface 420 and out through the outlet surface 430 (and, if coated, the portion of the permeable coating 470 at that surface 430) into the lumen 452. Oxygen would not diffuse radially through the other external surfaces of the anti-condensation filler 412 because of the nonpermeable coating 480.

In an example, the permeable coating 470 defines a permeable membrane made out of NuSil Technology LLC (of Carpinteria, Calif., U.S.A) MED4-4210, two-part medical grade silicone in which base and curing agent are mixed at a 10:1 ratio by weight. The thickness of this permeable membrane varies between 100 and 500 μm. For instance, the thickness is set to about 240 μm. In comparison, the nonpermeable coating 480 defines a nonpermeable material made out of parylene C. The thickness of this nonpermeable membrane varies within a range of two to twenty μm. For instance, the thickness is set to about five μm.

As indicated above, the sizes, shapes, and coatings of the collection and transport element 410 (including the anti-condensation filler 412), cannula 450, and discharge bag 460 can be set based on a targeted medical application. Some of the possible sizes, shapes, and coatings are further described in the next figures.

Figure 5:
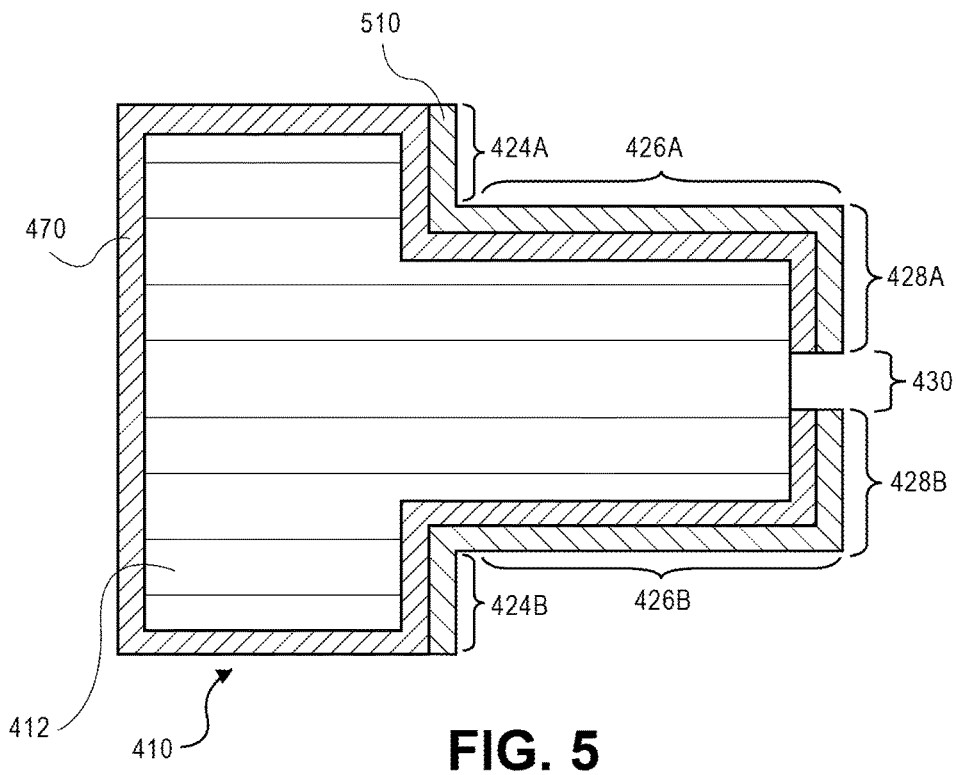
FIG. 5 illustrates a top view of a collection and transport element of an implantable medical device with a variation to its coatings, in accordance with an embodiment.

FIG. 5 illustrates a top view of the collection and transport element 410 of the implantable medical device 400 with a variation to its coatings, in accordance with an embodiment. In particular, the variation is to the nonpermeable coating 480. As illustrated, a nonpermeable coating 510 is deposited over the permeable coating 470 having locations corresponding to surfaces 424A and 424B, elongated surfaces 426A and 426B, and cannula-facing surfaces 428A and 428B, but not to the locations corresponding to the inlet surface 420, side surfaces 422A and 422B, shoulder, and outlet surface 430. As such, oxygen (or some other small molecules) can flow into the anti-condensation filler 412 through the inlet surface 420 and the side surface 422A and 422B and the corresponding portions of the permeable coating 470. In other words, the side surface 422A and 422B are set-up as additional inlet surfaces for oxygen.

Figure 6:
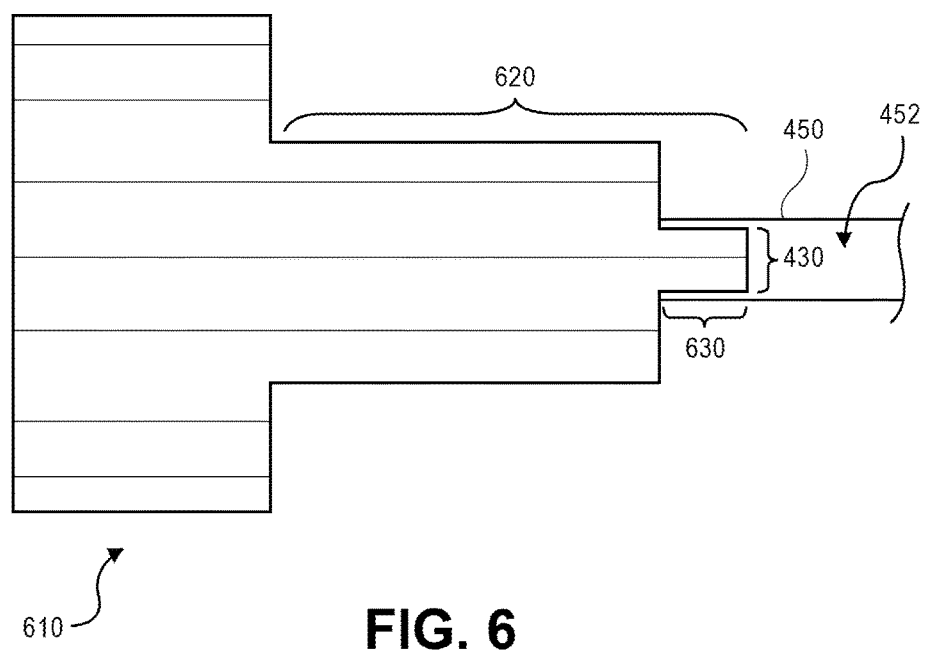
FIG. 6 illustrates a top view of an anti-condensation filler of an implantable medical device with a variation to its shape, in accordance with an embodiment.

FIG. 6 illustrates a top view of an anti-condensation filler 610, similar to the anti-condensation filler 412 of the implantable medical device 400 with a variation to its shape, in accordance with an embodiment. In particular, the variation is to how an elongated body 620 of the anti-condensation filler 610 interfaces with the cannula 450. As illustrated, the elongated body 620 extends from a base of the anti-condensation filler 610 and includes a protrusion 630 that is sized and shaped to be inserted in and mate with the cannula 450 (e.g., can fit into the lumen 452 and stay securely attached with the internal surface of the cannula 450 via mechanical friction and/or bonding, where the bonding may involve silicone). The outlet surface 430 is at an end of the protrusion 630, where this end faces and is in the lumen 452.

In an example, the cannula 450 has a cylindrical shape with a particular diameter that defines the lumen 452. In this example, the protrusion 630 also has a cylindrical shape with a slightly smaller diameter (e.g., 0.1 to five percent smaller). The height of this cylindrical protrusion 630 can be defined as a function of the height of the elongated body 620 (e.g., one to five percent) to support the secure attachment to the cannula 450.

Figure 7:
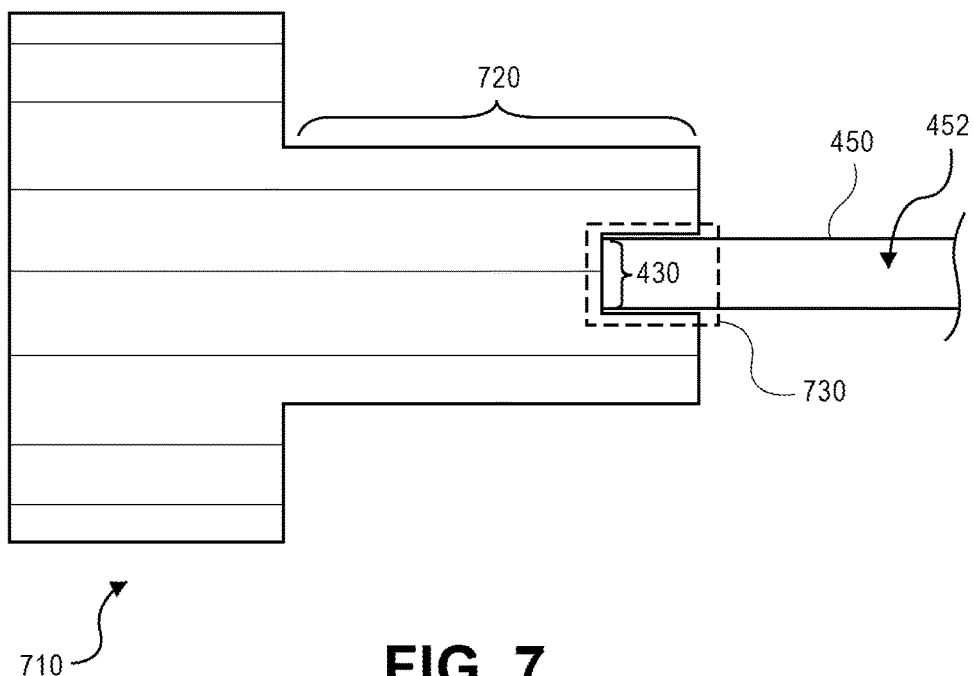
FIG. 7 illustrates a top view of the anti-condensation filler of an implantable medical device with another variation to its shape, in accordance with an embodiment.

FIG. 7 illustrates a top view of an anti-condensation filler 710, similar to the anti-condensation filler 412 of the implantable medical device 400 with another variation to its shape, in accordance with an embodiment. In particular, the variation is also to how an elongated body 720 of the anti-condensation filler 710 interfaces with the cannula 450. As illustrated, the elongated body 720 extends from a base of the anti-condensation filler 710 and includes a cavity 730 that is sized and shaped to receive and mate with the cannula 450 (e.g., the cannula 450 can fit into the cavity 730 and stay securely attached to it via mechanical friction and/or bonding, where the bonding may involve silicone). The outlet surface 430 is at an end of the cavity 730, where this end faces the lumen 452.

In an example, the cannula 450 has a cylindrical shape with a particular diameter that defines the lumen 452. In this example, the cavity 730 also has a cylindrical shape with a slightly larger diameter (e.g., 0.1 to five percent larger). The height of this cylindrical cavity 730 can be defined as a function of the height of the elongated body 720 (e.g., one to five percent) to support the secure attachment of the cannula 450.

Figure 8:
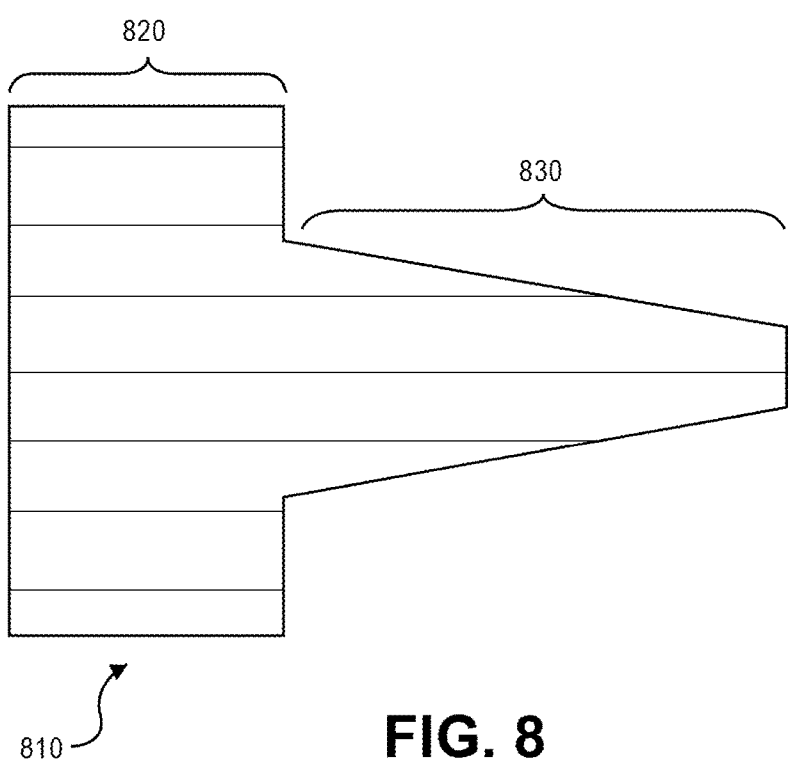
FIG. 8 illustrates a top view of anti-condensation filler of an implantable medical device with a different shape, in accordance with an embodiment.

FIG. 8 illustrates a top view of an anti-condensation filler 810 of the implantable medical device 400 with a different shape, in accordance with an embodiment. As illustrated, the anti-condensation filler 810 includes a base 820 and an elongated body 830. The base 820 has a substantially rectangular shape. In comparison, the elongated body 830 has substantially a cone shape.

Other variations are possible. For example, an anti-condensation filler can have a funnel shape, an L-shape, or other shapes. The base can be made to be of the same diameter and/or height as the elongated body. In an example, the anti-condensation filler may not include a base. In this example, the base may be replaced with an absorption or collection bag.

Figure 9:
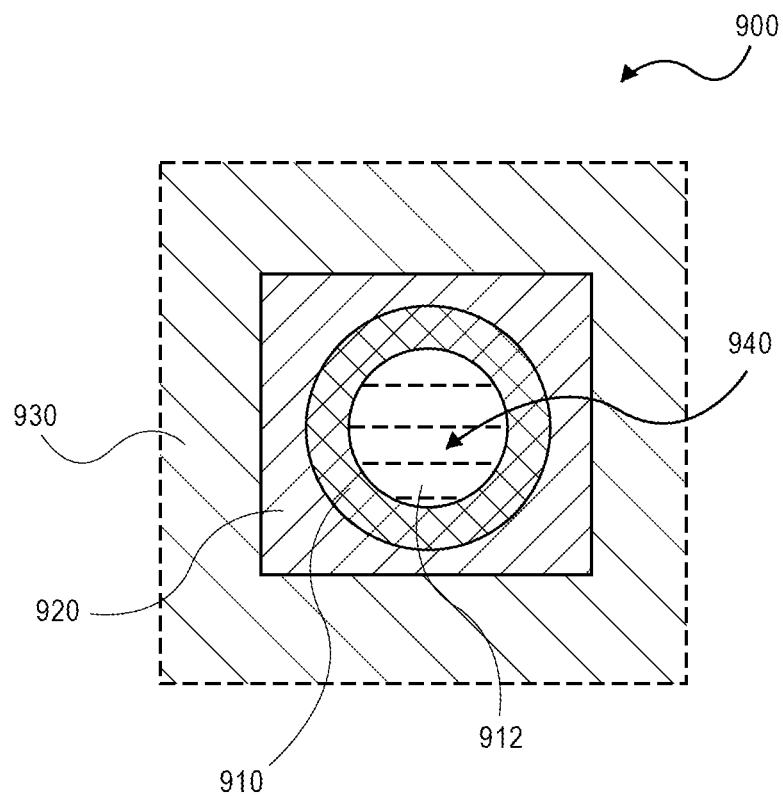
FIG. 9 illustrates a cross sectional view of a cannula of an implantable medical device, in accordance with an embodiment.

FIG. 9 illustrates a cross sectional view of a cannula 900 of an implantable medical device, such as the cannula 450 of the implantable medical device 400 of FIG. 4, in accordance with an embodiment. As illustrated, the cannula 900 includes a tube 910 that defines a lumen 912. A permeable coating 920 is deposited over an external surface of the tube 910 to form a permeable membrane. A nonpermeable coating 930 is deposited over an external surface of the permeable membrane. The tube 910 has an internal diameter of 406.4 μm and an outside diameter of 508 μm.

In an example, the cannula 900 is about twelve millimeters long with a width of about 1.3 millimeters. The permeable coating 920 surrounds the tube 910 and has an internal height of 720 μm with a ceiling and a floor thickness of 360 μm each, for a total thickness of 1440 μm. The side walls are 300 μm thick. The lumen 912 can contain a small molecule transport material 940 that is highly permeable to a predetermined class of small molecules (e.g., oxygen). For example, this material 940 can be any of a hydrophobized nano-porous material, expanded PTFE, PFC, and/or synthetic blood.

Figure 10:
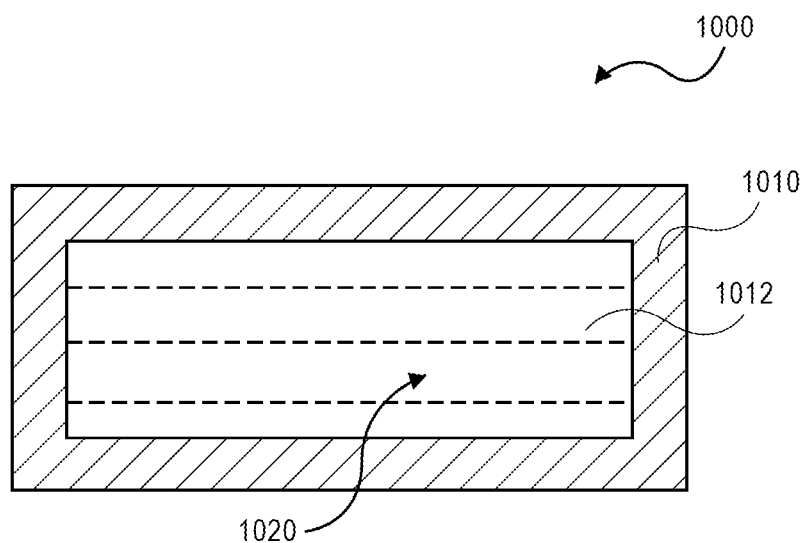
FIG. 10 illustrates a cross sectional view of a discharge bag of an implantable medical device, in accordance with an embodiment.

FIG. 10 illustrates a cross sectional view of a discharge bag 1000 of an implantable medical device, such as the discharge bag 460 of the implantable medical device 400 of FIG. 4, in accordance with an embodiment. As illustrated, the discharge bag 1000 includes a permeable membrane 1010 that defines walls, ceilings, and floors (or more generally a chamber, bag, or sac) containing an interior 1012. The interior 1012 can contain a small molecule transport material 1020 that is highly permeable to a predetermined class of small molecules (e.g., oxygen). For example, this material 1020 can be any of a hydrophobized nano-porous material, expanded PTFE, PFC, and/or synthetic blood.

Figure 11:
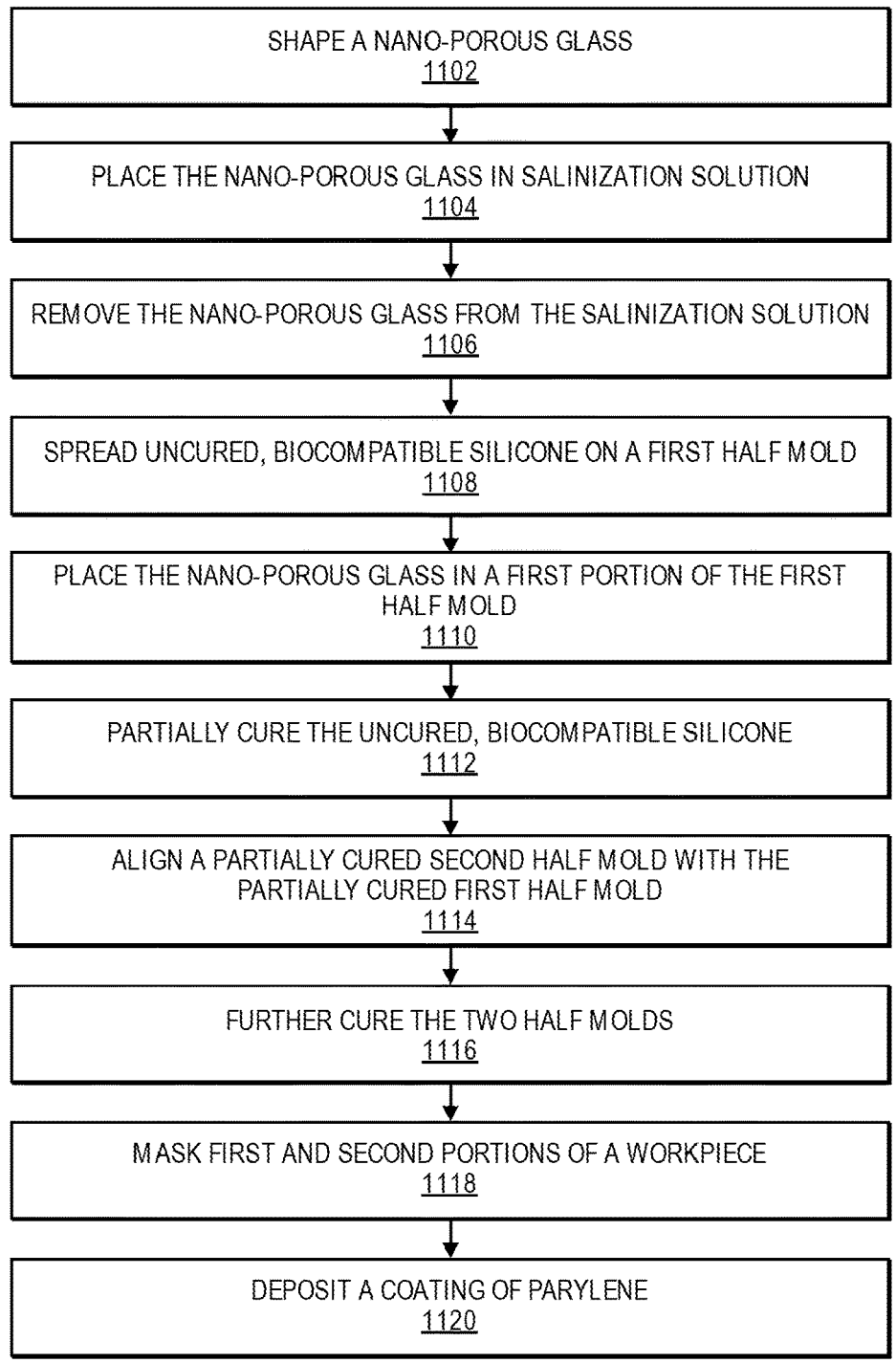
FIG. 11 is a flowchart illustrating a process for manufacturing an implantable medical device, in accordance with an embodiment.

FIG. 11 is a flowchart illustrating a process 1100 for manufacturing an implantable medical device, in accordance with an embodiment. The implantable medical device includes a collection and transport element, a cannula, and a small molecule discharge bag similarly to any of the implantable medical devices described herein above. In the interest of clarity of explanation, the collection and transport element is illustrated as including a nano-porous glass that is hydrophobized based on silanization, a cannula that includes a stainless steel tube, and a discharge back that is made out of a permeable material. However, other variations to the implantable medical device are possible and applicable manufacturing operations are apparent to a person of ordinary skill in the art in light of the present disclosure.

In operation 1102, a nano-porous glass is shaped into a predetermined shape that includes, for example, a base and an elongated body extending from the base. The shape and dimensions can depend on the targeted application of the implantable medical device. In an example, the nano-porous glass is Vycor 7930. A Vycor 7930 rod is shaped into a T-shaped tack through mechanical and/or chemical cutting or etching. The height and diameter of the base are about one millimeter and 3.7 millimeters, respectively. The height and diameter of the elongated body are about three millimeters and 1.5 millimeters, respectively. The base and the elongated body are centered around a same axis.

In operation 1104, the nano-porous glass is placed in a silanization solution for hydrophobization. In an example, this operation includes cleaning the nano-porous glass. For instance, this glass is cleaned in a Piranha solution of 3 parts nitric acid to 1 part hydrogen peroxide (30%) to remove organic material deposited on the large internal surface area of the glass. The cleaning can be performed at about eighty degrees Celsius until substantial bubble generation ceases, indicating the organics were removed, for approximately two hours. At this point the Piranha solution can be exchanged for fresh Piranha solution and the cleaning is further performed for about another hour to ensure that the reaction was not hydrogen peroxide limited. After this initial stage of cleaning, operation 1104 also includes placing the nano-porous glass in deionized water and incubated for about three hours at about ninety-five degrees Celsius, with hourly water changes to remove residual acid from within the pore network of the glass. Thereafter, operation 114 further includes placing the nano-porous glass in a clean, glass container fed with nitrogen boil-off to provide a clean atmosphere in which the glass could dry. The container can be heated to about ninety-five degrees Celsius to accelerate the drying process. At this point, the nano-porous glass has been cleaned. Operation 114 also includes hydrophobizing the cleaned glass via silanization. For example, the nano-porous glass is silanized by placing it in a sealed container containing an open vial of about one millimeter of either hexamethyldisilazane (HMDS) or dimethyldichlorosilane (DCDMS) (e.g., the silanization solution). Accordingly, silanization occurs through the vapor phase and is allowed to proceed for about twenty-four hours at room temperature.

In operation 1106, the nano-porous glass is removed from the silanization solution. In an example, the nano-porous glass is removed from the silanization containers and placed in an oven to bake at about one hundred and twenty degrees Celsius for about six hours. Operation 1106 can also include coating the nano-porous glass that was hydrophobized with a thin layer of polydimethylsiloxane (PDMS), such as MED 4210 and curing at about one hundred degrees Celsius overnight to protect the glass from fouling.

In operation 1108, uncured, biocompatible silicone is spread on a first half mold. Suitable silicone includes NuSil Technology LLC (of Carpinteria, Calif., U.S.A.) MED4-4210, two-part medical grade silicone in which base and curing agent are mixed at a 10:1 ratio by weight.

In operation 1110, the nano-porous glass is placed in a first portion of the first half mold. In an example, the first half mold includes three portions. The First portion corresponds to half of the collection and transport element. A second portion and a third portion correspond to half of the cannula and half of the discharge bag, respectively. Operation 1110 can also include placing the stainless steel tube of the cannula in the second portion of the first half mold. This tube is aligned such that one of its ends is in contact or close proximity to an outlet surface on the elongated body of the nano-porous glass.

In operation 1112, the uncured, biocompatible silicone placed on the first half mold that contains the nano-porous glass is partially cured. In an example, partial curing occurs while the nano-porous glass and the stainless steel tube are in place in the first half mold. The silicone is cured at about one hundred degrees Celsius for about five minutes.

In operation 1114, a partially cured second half mold is aligned with the partially cured first half mold that contains the nano-porous glass. In an example, the two halves have adjoining edges. The second half mold has also first, second, and third portions that correspond to the other halves of the collection and transport element, cannula, and discharge bag. These portions, like in operation 1108, contain silicone that has been partially cured, like in operation 1110. Uncured silicone can be applied to the adjoining edges. The uncured silicone is biocompatible and is used to adjoin the silicone half to a corresponding silicone half.

In operation 1116, the partially cured silicone halves, as aligned and adjoined, are further cured to create an integrally formed silicone workpiece. In an example, the curing is performed at about one hundred degrees Celsius for about three hours. The workpiece contains the nano-porous glass (surrounded by silicone; e.g., the collection and transport element), a sac (e.g., the discharge bag), and the cannula that connects the nano-porous glass and the sac. These parts are made of silicone and none of them is coated with parylene C at this point in the process. An extraction process can be applied to the cured silicone workpiece to remove any uncured elements. In an example, the extraction process includes soaking the cured silicone workpiece in an organic solvent, such as acetone, heptane, and/or hexane, over a period of time, such as a couple of days.

In operation 1118, a first portion and a second portion of the workpiece are masked. In an example, the first portion corresponds to at least an inlet surface of the base of the nano-porous glass, and the second portion corresponding to the sac.

In operation 1120, a coating of parylene C is deposited on the exterior surfaces of the workpiece. Because the first and second portions are masked, the parylene C coating does not render the inlet surface of the base or the sac (e.g., the discharge bag) nonpermeable.

Vycor 7930 that was hydrophobized according to operations 1102-1106 of the process 1400 was evaluated. In particular, evaluation of the capacity of the hydrophobized Vycor 7930 to resist condensation was carried out by placing one end of the rod in a heated water bath while blowing room temperature gas (nitrogen or oxygen) at one hundred percent relative humidity over the other end. The rod was shrink-wrapped circumferentially to restrict gas transport along the longitudinal direction. An oxygen probe was placed at the water-submerged end of the glass and the gas was stepped from nitrogen to oxygen and vice versa to measure the time constant of gas transport through the rod. The water bath temperature was varied from twenty-five to thirty seven to fifty degrees Celsius in order to test the material at progressively higher relative humidity. A non-silanized but otherwise identical Vycor 79300 glass was used as a negative control. The results of the experiment showed the time constant of gas transport through the silanized glass increased as a function of temperature whereas the time constant of gas transport through the non-silanized glass increased significantly at thirty-seven degrees Celsius. This result suggests that in the silanized glass, the pores remained sufficiently open despite internal relative humidity over one hundred percent. In contrast, it appears the pores of the non-silanized glass quickly filled with water from condensed vapor and became occluded thereby drastically slowing gas transport through the glass.

Additionally, the incorporation of hydrophobic fumed silica into PDMS was investigated to determine if the filler material could enhance gas transport and resist condensation. Six milliliters of hydrophobic fumed silica was incorporated into one gram of PDMS (MED 4210). The silicone was cured in a sheet of about one millimeter thick for permeability testing.

A COMSOL mass transport simulation was used for a four millimeters O.D. cylinder that is five millimeters in length. This cylinder was made of Vycor and covered in a thin layer of PDMS (one about one hundred microns) with a no flux condition on the radial perimeter, one atom of oxygen and one hundred percent relative humidity at the top (axial) side, and water at the bottom of the cylinder. This simulation was combined with a heat transport equation, working on direct conduction. Diffusivity and solubility of water vapor and thermal properties in water, Vycor, and PDMS were taken from literature. The simulation yielded the water vapor concentration in Vycor as well as the temperature distribution in the Vycor. The water temperature was swept from twenty-five to one hundred degrees Celsius resulting in a set of different vapor profiles. Using the empirical estimate for the saturation pressure based on temperature, the expected relative humidity was calculated by the ratio of the partial pressure of water vapor in Vycor to the saturation pressure in open air. This simulation also yielded an oxygen tension at the water end of the Vycor tube which was tested against the benchtop data.

Figure 12:
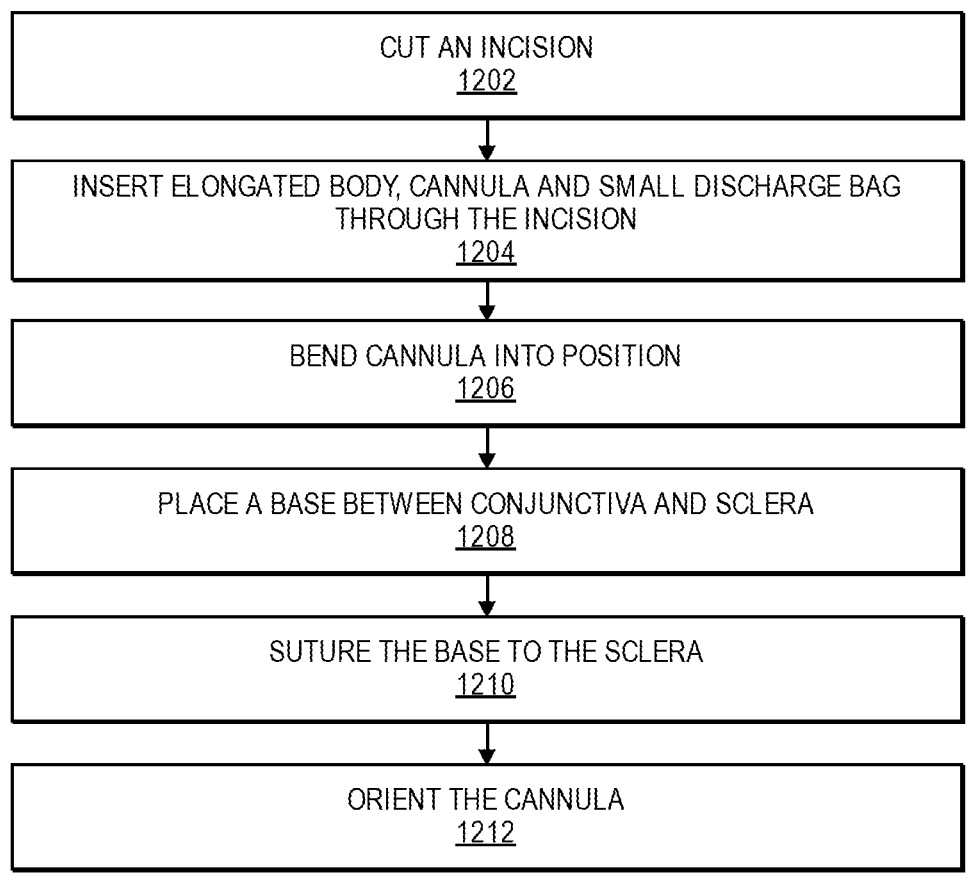
FIG. 12 is a flowchart illustrating a process for surgically implanting a medical device, in accordance with an embodiment.

FIG. 12 is a flowchart illustrating a process 1200 for surgically implanting a medical device, in accordance with an embodiment. In operation 1102, an implantable medical device is obtained. In an example, the implantable medical device includes a nano-porous glass, a small molecule discharge bag that includes an interior, and a cannula that includes a lumen connecting an elongated body of the nano-porous glass with the interior of the small molecule discharge bag. The nano-porous glass includes a base having a permeable coating over at least a portion of an external surface of the base and the elongated body extending from the base and having a nonpermeable coating over at least a portion of an external surface of the elongated body.

In operation 1202, an incision is cut through an eyeball of a subject, the incision being less than three millimeters long.

In operation 1204, the elongated body of the nano-porous glass, the cannula, and the small molecule discharge bag are inserted through the incision.

In operation 1208, the cannula is bent into position.

In operation 1210, the base of the nano-porous glass is placed between a conjunctiva and sclera of the eyeball.

In operation 1212, the base is sutured to the sclera.

In operation 1214, the cannula is oriented such that the discharge bag is within a posterior vitreous of the eyeball.

Although the process 1200 is illustrated in connection with implanting a medical device in an eyeball, embodiments of the present disclosure are not limited as such. Instead, the process 1200 can be similarly performed to implant anti-condensation filler across two environments with a humidity differential and/or a temperature differential. For example, an implantable medical device is obtained and includes an anti-condensation filler. The anti-condensation filler includes a nano-porous material that is hydrophobic or has been hydrophobized. A first portion of the anti-condensation filler is placed in a first environment. A second portion of the anti-condensation filler is placed in a second environment. The second environment has a higher humidity relative to the first environment. A temperature differential exists between the first environment and the second environment. In an illustrative use case, the first portion corresponds to a base of the anti-condensation filler and the second portion corresponds to an elongated body of the anti-condensation filler extending from the base. In this use case, the base is placed between a conjunctiva and sclera of an eyeball and the elongated body is placed inside the eyeball.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "Substantially" refers to more than 66%, 75%, 80%, 90%, 95%, or, depending on the context within which the term substantially appears, value otherwise as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A biocompatible, implantable medical device comprising:
   a collection and transport element comprising an anti-condensation filler, a permeable coating, and a nonpermeable coating, wherein:
      the anti-condensation filler is permeable to a predetermined class of small molecules and comprises a base and an elongated body extending from the base,
      the permeable coating is permeable to the small molecules and is over at least a portion of an external surface of the base,
      the nonpermeable coating is nonpermeable to the small molecules and is over at least a portion of an external surface of the elongated body;
   a cannula comprising a lumen; and
   a small molecule discharge bag comprising an interior, wherein at least a portion of the small molecule discharge bag is permeable to the small molecules.

2. The biocompatible, implantable medical device of claim 1, wherein the lumen of the cannula connects the elongated body of the anti-condensation filler with the interior of the small molecule discharge bag, wherein the anti-condensation filler comprises a nano-porous material, and wherein the predetermined class of small molecules comprises oxygen.

3. The biocompatible, implantable medical device of claim 2, wherein the nano-porous material comprises a nano-porous glass that is hydrophobized based on silanization, wherein the base and the elongated body are integrally formed with the nano-porous glass.

4. The biocompatible, implantable medical device of claim 3, wherein the nano-porous glass comprises pores having an average width determined based on the Kelvin Equation.

5. The biocompatible, implantable medical device of claim 4, wherein the average width is within a range of four to twenty nanometers, and wherein a density of the pores is in the range of twenty to fifty percent.

6. The biocompatible, implantable medical device of claim 1, wherein the base is substantially cylindrical and has a first height and a first diameter, wherein the elongated body is substantially cylindrical and has a second height and a second diameter, and wherein the first height is smaller than the second height and the first diameter is larger than the second diameter.

7. The biocompatible, implantable medical device of claim 6, wherein the first height is between 0.1 and two millimeters, and wherein the first diameter is between one and fifteen millimeters.

8. The biocompatible, implantable medical device of claim 6, wherein the second height is between one and twenty-five millimeters, and wherein the second diameter is between 0.05 and three millimeters.

9. The biocompatible, implantable medical device of claim 1, wherein the base and the elongated body are integrally formed in substantially a T-shaped tack, wherein the base corresponds to a cylindrical head of the T-shaped tack, and wherein the elongated body corresponds to a cylindrical shaft of the T-shaped tack.

10. The biocompatible, implantable medical device of claim 1, wherein the base and the elongated body are integrally formed, wherein the nonpermeable coating is over a remaining portion of the external surface of the base.

11. The biocompatible, implantable medical device of claim 10, wherein the external surface of the elongated body comprises an outlet surface, wherein the elongated body and an end of the cannula connect at the outlet surface, and the nonpermeable coating is over the external surface of the elongated body except for the outlet surface.

12. The biocompatible, implantable medical device of claim 11, wherein the permeable coating is beneath the nonpermeable coating and over the external surface of the elongated body except for the outlet surface.

13. The biocompatible, implantable medical device of claim 11, wherein additional nonpermeable coating is over an external surface of the cannula, and wherein additional permeable coating is over an external surface of the small molecule discharge bag.

14. The biocompatible, implantable medical device of claim 13, wherein the additional permeable coating is also over the external surface of the cannula and beneath the additional nonpermeable coating.

15. The biocompatible, implantable medical device of claim 1, wherein the base has a width larger than a width of the elongated body, and wherein the elongated body has a length larger than a length of the base.

16. The biocompatible, implantable medical device of claim 1, wherein the anti-condensation filler is made of a nano-porous glass, and wherein at least one of the cannula or the small molecule discharge bag comprises additional nano-porous glass.

17. The biocompatible, implantable medical device of claim 1, wherein the anti-condensation filler is made of a nano-porous glass, and wherein at least one of the cannula or the small molecule discharge bag comprises perfluorocarbon.

18. A method of manufacturing a biocompatible, implantable medical device, the method comprising:
   spreading uncured, biocompatible silicone on a first half mold;
   placing a nano-porous glass in a first portion of the first half mold, the nano-porous glass comprising a base and an elongated body extending from the base, the nano-porous glass hydrophobized based on silanization;
   partially curing the uncured, biocompatible silicone on the first half mold that contains the nano-porous glass;
   aligning a partially cured second half mold with the partially cured first half mold that contains the nano-porous glass;
   further curing the partially cured second half mold and the partially cured first half mold to create an integrally formed workpiece that contains the nano-porous glass, a sac, and a cannula that connects the nano-porous glass and the sac;
   masking a first portion and a second portion of the workpiece, the first portion corresponding to at least the base of the nano-porous glass, and the second portion corresponding to the sac; and
   depositing parylene on the workpiece.

19. A method of surgically implanting a biocompatible, implantable medical device, the method comprising:

obtaining the biocompatible, implantable medical device, the biocompatible, implantable medical device comprising:
- a collection and transport element comprising an anti-condensation filler, a permeable coating, and a non-permeable coating, wherein:
  - the anti-condensation filler is permeable to a predetermined class of small molecules and comprises a base and an elongated body extending from the base,
  - the permeable coating is permeable to the small molecules and is over at least a portion of an external surface of the base,
  - the nonpermeable coating is nonpermeable to the small molecules and is over at least a portion of an external surface of the elongated body;
- a cannula comprising a lumen; and
- a small molecule discharge bag comprising an interior, wherein at least a portion of the small molecule discharge bag is permeable to the small molecules;

placing the base of the anti-condensation filler in a first environment; and placing the elongated body of the anti-condensation filler in a second environment, wherein the second environment has a higher humidity relative to the first environment, and wherein a temperature differential exists between the first environment and the second environment.

20. The method of claim 19, wherein the base is placed between a conjunctiva and sclera of an eyeball, and wherein the elongated body is placed inside the eyeball.

* * * * *